United States Patent
Watson, Jr.

(10) Patent No.: US 7,824,384 B2
(45) Date of Patent: Nov. 2, 2010

(54) CHEST TUBE DRAINAGE SYSTEM

(75) Inventor: Richard L. Watson, Jr., McPherson, KS (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

(21) Appl. No.: 11/200,837

(22) Filed: Aug. 10, 2005

(65) Prior Publication Data
US 2006/0036221 A1    Feb. 16, 2006

Related U.S. Application Data

(60) Provisional application No. 60/600,229, filed on Aug. 10, 2004.

(51) Int. Cl.
A61F 13/00    (2006.01)
A61M 1/00    (2006.01)

(52) U.S. Cl. ............... 604/313; 604/305; 604/317; 604/319

(58) Field of Classification Search ........... 604/313, 604/315, 317–327, 386, 387, 540–544; 600/573, 600/576, 581
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,376,868 A | 4/1968 | Mondiadis |

(Continued)

FOREIGN PATENT DOCUMENTS

AU    550575 A1    8/1982

(Continued)

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(Continued)

*Primary Examiner*—Melanie J Hand (57) ABSTRACT

A system for draining the chest cavity of a patient subjected to a traumatic chest injury and/or to surgery within the chest. The system includes a small, portable suction device and a chest tube with an improved terminal structure. A number of embodiments of the suction device are disclosed; the first (with two variations) a small, completely disposable, bottle-shaped assembly comprising a motor/pump section, a power section, and a desiccant filled chamber, the second (also with two variations) a small box shaped assembly with a disposable desiccant pouch and a power supply that mounts to a battery charger positioned on an IV pole. A number of chest tube terminus structures are disclosed, including multi-lumen structures having high-airflow and low-airflow lumens as well as "dead" and "live" lumens. Fenestrations are variously positioned between and through the lumens in order to collect coagulated components of the extracted fluids and prevent them from clogging the primary flow tube and restricting or preventing continuous airflow.

35 Claims, 10 Drawing Sheets

U.S. PATENT DOCUMENTS

| | | |
|---|---|---|
| 3,382,867 A | 5/1968 | Reaves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,779,243 A | 12/1973 | Tussey et al. |
| 3,823,716 A | 7/1974 | Hale |
| 3,826,254 A | 7/1974 | Mellor |
| 3,875,941 A | 4/1975 | Adair |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,329,743 A | 5/1982 | Alexander et al. |
| 4,333,468 A | 6/1982 | Gelst |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,433,973 A * | 2/1984 | Kurtz et al. ................ 604/403 |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielson |
| 4,640,688 A | 2/1987 | Hauser |
| 4,642,093 A | 2/1987 | Härle |
| 4,643,719 A | 2/1987 | Garth et al. |
| 4,655,754 A | 4/1987 | Richmond et al. |
| 4,664,652 A | 5/1987 | Weilbacher |
| 4,664,662 A | 5/1987 | Webster |
| 4,681,570 A | 7/1987 | Dalton |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,981,474 A | 1/1991 | Bopp et al. |
| 4,985,019 A | 1/1991 | Michelson |
| 5,013,300 A | 5/1991 | Williams |
| 5,019,059 A | 5/1991 | Goldberg et al. |
| 5,034,006 A | 7/1991 | Hosoda et al. |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,102,404 A | 4/1992 | Goldberg et al. |
| 5,112,323 A | 5/1992 | Winkler et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,259,399 A | 11/1993 | Brown |
| 5,261,893 A | 11/1993 | Zamierowski |
| 5,266,071 A | 11/1993 | Elftman |
| 5,278,100 A | 1/1994 | Doan et al. |
| 5,279,550 A | 1/1994 | Habib et al. |
| 5,298,015 A | 3/1994 | Komatsuzaki et al. |
| 5,324,306 A | 6/1994 | Makower et al. |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,405,322 A | 4/1995 | Lennox et al. |
| 5,437,622 A | 8/1995 | Carion |
| 5,437,651 A | 8/1995 | Todd et al. |
| 5,470,316 A | 11/1995 | Tovey et al. |
| 5,527,293 A | 6/1996 | Zamierowski |
| 5,549,579 A | 8/1996 | Batdorf et al. |
| 5,549,584 A | 8/1996 | Gross |
| 5,556,375 A | 9/1996 | Ewall |
| 5,569,184 A | 10/1996 | Crocker et al. |
| 5,607,388 A | 3/1997 | Ewall |
| 5,636,643 A * | 6/1997 | Argenta et al. .............. 128/897 |
| 5,643,589 A * | 7/1997 | Chalmers .................... 424/404 |
| 5,645,081 A | 7/1997 | Argenta et al. |
| 5,676,634 A | 10/1997 | Khouri |
| 5,713,874 A | 2/1998 | Ferber |
| 5,735,833 A | 4/1998 | Olson |
| 5,762,640 A | 6/1998 | Kajiwara et al. |
| 5,820,581 A | 10/1998 | Wolfinbarger, Jr. |
| 5,914,264 A | 6/1999 | Korman |
| 5,941,859 A | 8/1999 | Lerman |
| 5,984,942 A | 11/1999 | Alden et al. |
| 6,042,537 A | 3/2000 | Kaiser |
| 6,071,267 A | 6/2000 | Zamierowski |
| 6,080,243 A | 6/2000 | Insley et al. |
| 6,135,116 A | 10/2000 | Vogel et al. |
| 6,142,982 A | 11/2000 | Hunt et al. |
| 6,174,306 B1 | 1/2001 | Fleischmann |
| 6,241,747 B1 | 6/2001 | Ruff |
| 6,287,316 B1 | 9/2001 | Agarwal et al. |
| 6,345,623 B1 | 2/2002 | Heaton et al. |
| 6,394,948 B1 | 5/2002 | Borst et al. |
| 6,398,767 B1 | 6/2002 | Fleischmann |
| 6,458,109 B1 | 10/2002 | Henley et al. |
| 6,478,789 B1 | 11/2002 | Spehalski et al. |
| 6,488,643 B1 | 12/2002 | Tumey et al. |
| 6,493,568 B1 | 12/2002 | Bell et al. |
| 6,500,112 B1 | 12/2002 | Khouri |
| 6,551,280 B1 | 4/2003 | Knighton et al. |
| 6,553,998 B2 | 4/2003 | Heaton et al. |
| 6,572,594 B2 | 6/2003 | Satterfield et al. |
| 6,626,891 B2 | 9/2003 | Ohmstede |
| 6,641,553 B1 | 11/2003 | Chee |
| 6,641,575 B1 | 11/2003 | Lonky |

| | | | |
|---|---|---|---|
| 6,648,862 B2 * | 11/2003 | Watson | 604/319 |
| 6,656,149 B2 | 12/2003 | Ladd | |
| 6,660,484 B2 | 12/2003 | Charch et al. | |
| 6,682,506 B1 | 1/2004 | Navarro | |
| 6,685,681 B2 | 2/2004 | Lockwood et al. | |
| 6,695,823 B1 | 2/2004 | Lina et al. | |
| 6,752,794 B2 | 6/2004 | Lockwood et al. | |
| 6,755,796 B2 | 6/2004 | Spector | |
| 6,755,807 B2 | 6/2004 | Risk, Jr. et al. | |
| 6,758,836 B2 | 7/2004 | Zawacki | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,840,960 B2 | 1/2005 | Bubb | |
| 6,855,135 B2 | 2/2005 | Lockwood et al. | |
| 6,979,324 B2 | 12/2005 | Bybordi et al. | |
| 7,004,915 B2 | 2/2006 | Boynton et al. | |
| 7,022,113 B2 | 4/2006 | Lockwood et al. | |
| 7,070,584 B2 | 7/2006 | Johnson et al. | |
| 7,077,832 B2 | 7/2006 | Fleischmann | |
| 7,128,735 B2 | 10/2006 | Weston | |
| 7,195,624 B2 | 3/2007 | Lockwood et al. | |
| 7,276,051 B1 | 10/2007 | Henley et al. | |
| 7,344,512 B2 | 3/2008 | Yamazaki | |
| 7,396,339 B2 | 7/2008 | Britto et al. | |
| 2002/0065494 A1 | 5/2002 | Lockwood et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0198504 A1 | 12/2002 | Risk, Jr. et al. | |
| 2003/0088209 A1 | 5/2003 | Chiu et al. | |
| 2003/0187367 A1 * | 10/2003 | Odland | 600/573 |
| 2003/0216672 A1 | 11/2003 | Rastegar et al. | |
| 2003/0225441 A1 | 12/2003 | Boynton et al. | |
| 2004/0006319 A1 | 1/2004 | Lina et al. | |
| 2004/0039406 A1 * | 2/2004 | Jessen | 606/167 |
| 2004/0064111 A1 | 4/2004 | Lockwood et al. | |
| 2004/0064132 A1 | 4/2004 | Boehringer et al. | |
| 2004/0093026 A1 | 5/2004 | Weidenhagen et al. | |
| 2005/0004534 A1 | 1/2005 | Lockwood | |
| 2005/0065484 A1 | 3/2005 | Watson, Jr. | |
| 2005/0070858 A1 | 3/2005 | Lockwood et al. | |
| 2005/0131327 A1 | 6/2005 | Lockwood et al. | |
| 2005/0137539 A1 * | 6/2005 | Biggie et al. | 604/313 |
| 2005/0171467 A1 * | 8/2005 | Landman | 604/35 |
| 2005/0203483 A1 | 9/2005 | Perkins et al. | |
| 2005/0245906 A1 | 11/2005 | Makower et al. | |
| 2005/0261642 A1 | 11/2005 | Weston | |
| 2005/0261643 A1 | 11/2005 | Bybordi et al. | |
| 2006/0149170 A1 | 7/2006 | Boynton et al. | |
| 2007/0021698 A1 | 1/2007 | Fleischmann | |
| 2007/0118096 A1 | 5/2007 | Smith et al. | |
| 2008/0275409 A1 | 11/2008 | Kane et al. | |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 03/057070 A2 | 7/2003 |
| WO | WO 2005/105180 A1 | 11/2005 |
| WO | WO 2007/133618 A2 | 11/2007 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation, Apr. 21, 2007.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concers all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Spit-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transpoantation, vol. 7, 1979, p. 221.

Svedman, P. et al: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

International Search Report and Written Opinion for PCT/US07/03065; date mailed Jul. 28, 2008.

Marc G. Jeschke, MD, et al: "Development of New Reconstructive Techniques: Use of Integra in Combination with Fibrin Glue and Negaitve-Pressure Therapy for Reconstruction of Acute and Chronic Wounds"; Plastic and Reconstructive Surgery, Feb. 2004, vol. 113, No. 2, pp. 525-530.

C. Daniel Medical, Inc.; All Silicone Jackson Pratt® Style Round Drain; www.cdanielmedical.com; Mar. 2007, 2 pgs.

C. Daniel Medical, Inc.; All Silicone Jackson Pratt® Style Flat Drain; www.cdanielmedical.com; Mar. 2007, 2 pgs.

Non-Final Office Action dated Jun. 12, 2008 for U.S. Appl. No. 11/702,822.

Response filed Jul. 14, 2008 for Non-Final Office Action dated Jun. 12, 2008 for U.S. Appl. No. 11/702,822.

Non-Final Office Action dated Aug. 26, 2008 for U.S. Appl. No. 11/702,822.

Response filed Nov. 13, 2008 to Non-Final Office Action dated Aug. 26, 2008 for U.S. Appl. No. 11/702,822.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Australian Examiner's Report dated Apr. 6, 2009; Australian Patent Application No. 2007212480.

Notice of Allowance dated Apr. 16, 2009 for U.S. Appl. No. 11/702,822.

NPD 1000 Negative Pressure Wound Therapy System, Kalypto Medical, pp. 1-4.

V.A.C.® Therapy Clinical Guidelines: A Reference Source for Clinicians (Jul. 2007).

Non-Final Office Action date mailed Jun. 18, 2009 in U.S. Appl. No. 11/807,834.

Response filed Aug. 19, 2009 to Non-Final Action dated Jun. 18, 2009 in U.S. Appl. No. 11/807,834.

Final Rejection date mailed Oct. 2, 2009 in U.S. Appl. No. 11/807,834.

RCE/Amendment filed Jan. 27, 20110 in U.S. Appl. No. 11/807,834.

Non-Final Rejection date mailed Mar. 11, 2010 in U.S. Appl. No. 11/807,834.

Restriction Requirement date mailed Apr. 13, 2010 in U.S. Appl. No. 12/069,363.

Express Abandonment filed Apr. 22, 2010 in U.S. Appl. No. 12/540,934.

Response to Restriction Requirement mailed May 4, 2010 in U.S. Appl. No. 12/069,363.

Decision on Petition for Express Abandonment date and Notice of Abandonment date mailed May 3, 2010 in U.S. Appl. No. 12/540,934.

Interview Summary date mailed Jun. 11, 2010 in U.S. Appl. No. 11/807,834.

Response filed Jun. 14, 2010 to Non-Final Rejection date mailed Mar. 11, 2010 in U.S. Appl. No. 11/807,834.

Non-Final Office Action date mailed Jul. 9, 2010 in U.S. Appl. No. 12/069,363.

International Search Report and Written Opinion date mailed Jun. 28, 2010 in PCT/US2009/064972.

* cited by examiner

Fig. 18

CHEST TUBE DRAINAGE SYSTEM

This application is based upon and claims priority from U.S. Provisional application Ser. No. 60/600,229, filed Aug. 10, 2004, which is incorporated herein by reference.

BACKGROUND OF THE INVENTION

1. Field of the Invention

The present invention relates generally to medical and surgical devices and systems that serve to remove air and fluids from the body of a patient after injury or during and after surgery. The present invention relates more specifically to a system for use in association with the removal of air and fluids from the chest cavity of a patient during surgery or as a manner of treatment for a chest injury.

2. Background Information

The human chest cavity is lined with membranes referred to as the parietal pleura and the visceral pleura. The parietal pleura line the chest cavity itself, while the viscera pleura are the membranes that line the lungs. The space between the two membranes is called the intrapleural space (or sometimes simply "the pleural space") that normally has a small amount of fluid within it in a healthy individual. This fluid is drained and regulated by the lymphatic system and provides lubrication and cohesion between the pleura for normal lung function.

An individual may accumulate air, fluid, or purulent drainage in the intrapleural space due to a number of pathologic conditions. When blood accumulates in this space, the condition is referred to as a hemothorax; air accumulation in the space is referred to as a pneumothorax; and purulent drainage accumulating in that space is referred to as empyema. Under such conditions as these, chest tubes may be required to provide drainage of air and excess fluid of any type. Excess fluid in the intrapleural space may be caused by liver or kidney failure, congestive heart failure, infection, malignancy blocking the lymphatic system, trauma, or other injury to the lungs or chest cavity. If the amount of fluid is very small, chest tubes would not typically be necessary. However, if a considerable amount of fluid or blood that cannot be absorbed by the body itself is present, chest tubes and a drainage system will typically be required. Similar conditions may exist within the intrapleural space during and after surgical intervention into the chest cavity.

When there is an excess amount of fluid or air in the pleural space, simply having an open airway will not typically result in sufficient air exchange for the patient due to the likely presence of a partial or complete lung collapse. A lung collapse occurs when the pressure in the intrapleural space is altered by the excess air or fluid accumulation presses inward on the lung causing it to collapse. Normally, the intrapleural pressure is below atmospheric pressure, thus allowing the lung to easily expand. When a lung does collapse, chest tubes may be used to allow drainage of the air or fluid and restore normal pressure to the intrapleural space so the lungs can expand and adequate gas exchange will occur. Such chest tubes inserted into the pleural space are typically attached to a drainage system that is closed to the atmosphere and is often maintained at sub-atmospheric pressure so as to create suction.

Depending on the condition of the patient, a chest tube may be inserted and maintained at the patient's bedside, in an ambulance, or in an operating room. The positioning of a chest tubes and the point of insertion will depend in part upon the type of fluid which has accumulated in the intrapleural space.

Previous efforts to provide chest tube drainage systems have typically utilized gravity and suction to evacuate the excess fluids and air. The typical closed chest drainage system is maintained at a level lower than that of the patient in order for gravity to facilitate fluid drainage from the intrapleural space. Suction may also be used to promote the transfer of air or fluid out of the intrapleural cavity.

The traditional drainage system of the prior art involved the use of one, two, or three bottle pleural drainage systems. Each of these systems operated under the basic principles of gravity, positive pressure, and suction, with the one bottle system being the simplest, yet most difficult to monitor. The two bottle system required less vigilance with respect to fluid level monitoring, whereas the three bottle pleural drainage system enabled suction control. Most modern facilities now use a disposable (or partially disposable) pleural drainage system that combines suction control, fluid collection, and a water seal into one multi-chambered unit. These are simply three chambered systems that use the same principles as the classic three bottle system. Examples of such systems are described in U.S. Pat. Nos. 4,784,642, 4,769,019 and 4,354,493.

Several difficulties arise with systems heretofore described in the art, including the kinking of the tubing, the formation of clots and blockages, problems with the suction, and problems with dependent loops (air and fluid) in the tubing. Additionally, the classic bottle systems, even those that involve an integrated three chamber structure, are typically quite bulky and do not allow easy transportation or ambulation of the patient. Although some integrated systems have been developed that are directed to being lightweight, portable, non-breakable, and disposable, many problems with the collection tubing still exist. Additionally, these types of devices typically must be connected to large pump systems or stationary vacuum sources which decrease or altogether eliminate their portability.

A problem almost universally encountered within the prior art is the inadequate drainage of the intrapleural space due to clots or gelatinous inflammatory material and the resultant plugging or kinking of the tube. Another frequent problem in the prior art is the disposal of the biohazardous fluids from the drainage collection chambers. While the chambers may be sealed during use it is often necessary to expose the health care provider to the collected fluids during the removal and disposal process.

SUMMARY OF THE INVENTION

The present invention provides a system for draining the chest cavity of a patient subjected to a traumatic chest injury and/or subjected to surgical procedures within the chest cavity. The system includes a small, portable suction device and a chest tube with an improved terminal structure. Two embodiments of the suction device are disclosed. The first embodiment of the suction device is a small, completely disposable, bottle shaped assembly comprising a motor/pump section, a power section, and a desiccant chamber. The second suction device embodiment is a small box shaped assembly with a disposable desiccant pouch. This second configuration of the suction device can be mounted to a battery charger that may in turn be positioned on an IV pole.

A number of chest tube terminal structures for insertion into the pleural space of a patient are disclosed in the system of the present invention, including multi-lumen structures having both high-airflow and low-airflow lumens. Fenestrations in the form of small slits or the like in the tubular walls are variously positioned between the lumens and between the interior and exterior spaces defined by the lumens, in order to collect coagulated components of the extracted fluids and facilitate the maintenance of a continuous flow of air.

Further, system of the present invention lends itself to the incorporation of a variety of sensors in the chest tube, the chest tube terminus, and/or the suction device. These sensors may include any of a number of pressure monitoring devices, differential pressure devices, flow rate meters, fluid/gas mixture transducers, and blood saturation monitors.

DETAILED DESCRIPTION OF THE PREFERRED EMBODIMENT

1. The Suction Pump and Desiccant Container

Figure 1:
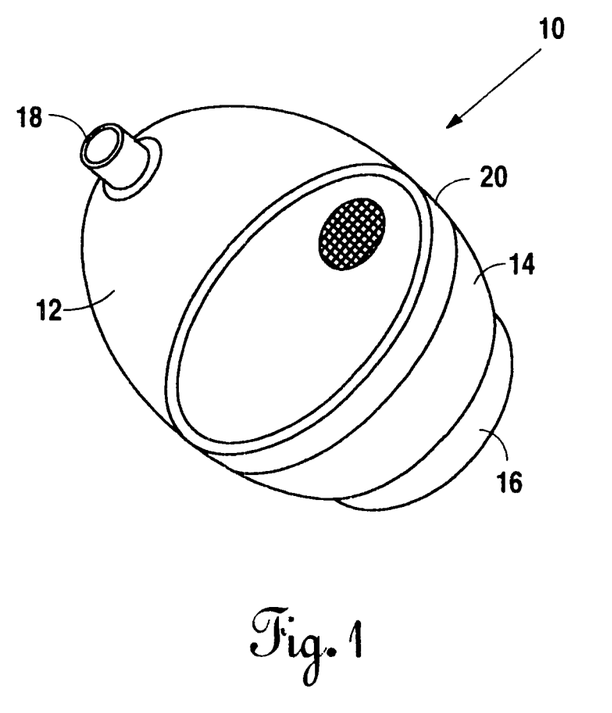
FIG. 1 is a perspective view of a first structural embodiment of the suction device component of the system of the present invention.

As summarized above, the present invention is directed to a system for sucking air and excess fluid out of the chest cavity of a patient during and after surgical operations, as well as in response to a chest injury such as, for example, a collapsed lung. FIG. 1 discloses one critical element of a first preferred system embodiment of the present invention, comprising a suction device 10 having a motor/pump section 14, a power section 16, and a desiccant chamber section 12 in operative communication with each other. Desiccant chamber 12 preferably incorporates chest tube connection 18, which in the preferred embodiment may be a screw-on, or quick connect fitting, for connection to a chest tube (not shown), the other end of which is adaptable for placement in the chest cavity as described in more detail below. Desiccant chamber 12 is preferably constructed of a clear, high impact plastic and is removable from power section 16 and motor/pump section 14 at disconnection point 20 and is replaceable in a like manner. Desiccant chamber 12 contains a desiccant material (not shown in this view) for absorbing liquids, such as blood, that are sucked out of the chest cavity along with the air. Desiccant chamber 12 preferably contains anti-microbial and/or anti-bacterial chemicals, which are preferably chlorine-based, to render the suctioned materials non-bio-hazardous. Although FIG. 1 shows for illustration the power section 16 located at the base of the motor/pump section 14, the power section 16 may be placed in any other desired location including without limitation between the desiccant chamber 12 and the motor/pump section 14, and on the inside or outside (or a combination of both) of the suction device 10.

Figure 2:
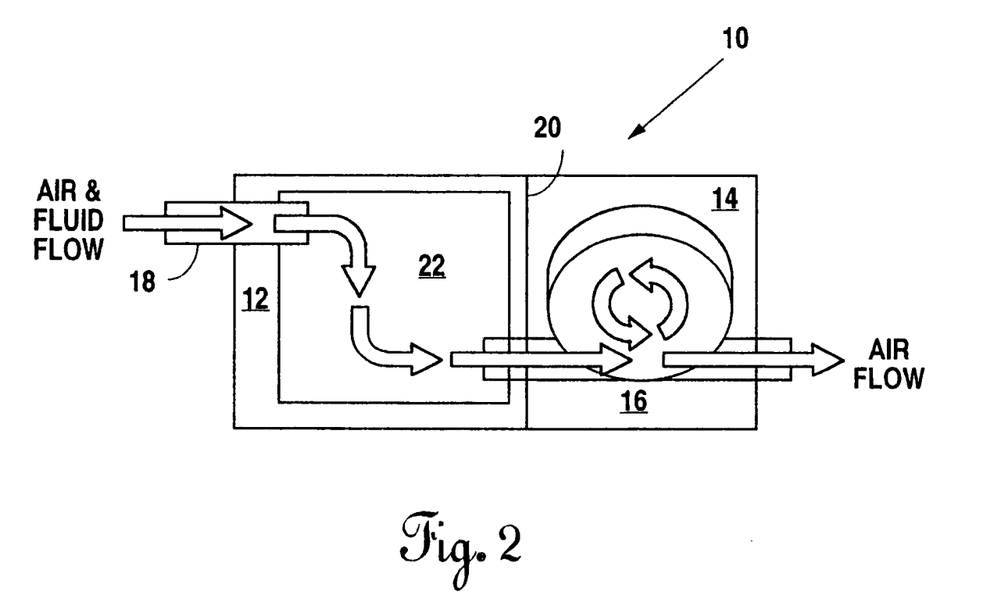
FIG. 2 is a schematic functional diagram of the first structural embodiment of the suction device component of the system of the present invention.

FIG. 2 discloses in schematic form the basic functional components of the suction device of the system of the present invention, as characterized in each of the preferred embodiments described. Suction device 10 comprises motor/pump section 14 and power section 16 connected to desiccant chamber 12 at disconnection point 20. Airflow is directed through the device from chest tube connection 18 (wherein the air flow may include fluid flow) into desiccant chamber 12 wherein fluids in the airflow are absorbed into desiccant material 22. An electrically driven motor (powered by power section 16) turns an air pump within motor/pump section 14 to direct the air flow from desiccant chamber 12 and out from the device.

Figure 3:
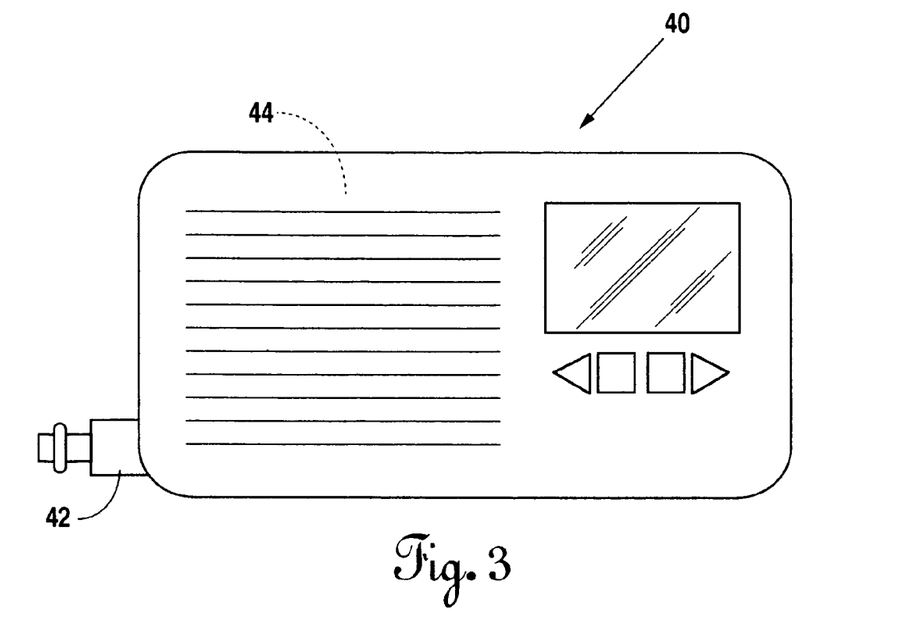
FIG. 3 is a front view of a second structural embodiment of the suction device component of the system of the present invention.
Figure 4:
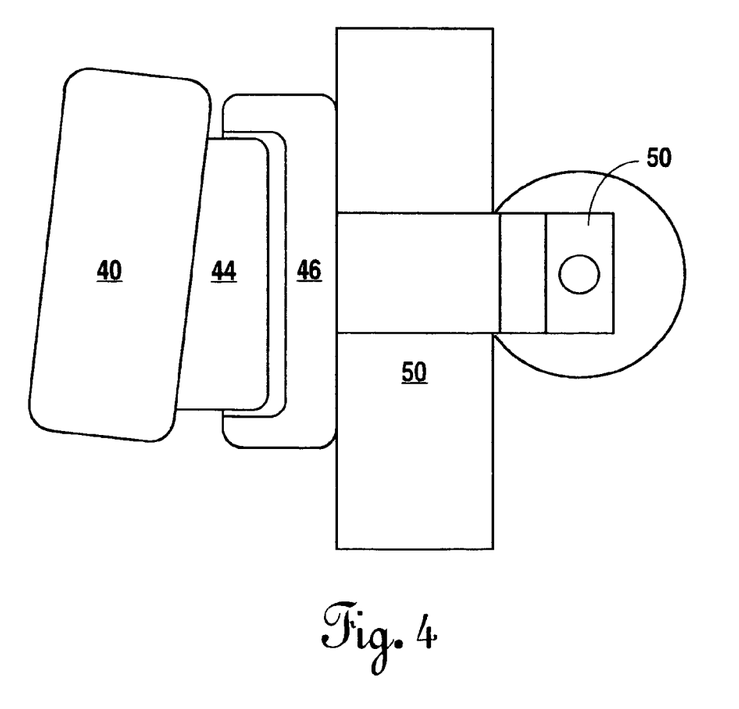
FIG. 4 is a side view of the second structural embodiment of the suction device component of the system of the present invention, shown attached to an IV pole.

An alternative preferred embodiment of the suction device of the system of the present invention is shown in FIGS. 3 & 4. This embodiment of suction device 40 may be mounted on an IV pole 50 as illustrated in FIG. 4. This embodiment of suction device 40 incorporates chest tube connection 42 and preferably has a disposable desiccant pouch 44 (hidden in these views within the device enclosure) as disclosed and described in U.S. Pat. No. 6,648,862, the disclosure of which is incorporated in its entirety herein by reference. As illustrated in FIG. 4, a power charging unit 46 is preferably clipped to IV pole 50 by way of bracket 52. Suction device 40 incorporates chargeable power supply 44 which in turn attaches, clips, plugs into or otherwise connects into power charging unit 46 as shown.

The first embodiment of the suction device of the present invention described above with respect to FIGS. 1 & 2 may be constructed small enough and of readily available materials and components as to allow the unit to be completely disposable (i.e. a single patient, single use device). The desiccant chamber section (12 in FIG. 1) may be replaced as needed for a particular patient while the entire device might be disposed of after use is completed for the particular patient.

The first embodiment of the suction device of the present invention described above may also find application in other medical situations not involving chest tube placement and drainage. The low vacuum device could, for example, be utilized as a very small wound pump to provide a sub-atmospheric pressure on a healing wound as has become beneficially evident in the wound treatment field. The airflow volume required for a chest tube pump would generally be higher, and the volume required for a wound pump generally lower. Variations in the airflow generated by this variation of the suction device component of the system of the present invention could be achieved through known methods of modifying the pump rate by way of modifying the motor speed. These variations could be implemented as "hard wired" flow rates through preset electronic/electrical parameters, or as variable flow rates through the use of variable electronic/electrical components in the motor controller circuitry.

The second embodiment of the suction device of the present invention described above with respect to FIGS. 3 & 4 would be constructed in a manner similar to the device described in the referenced U.S. Pat. No. 6,648,862. In so far as the device described in this referenced U.S. Patent is primarily directed to the wound healing arts, the structure of a similar device appropriate for use with chest drainage would require modifications that would increase the airflow volume through the device and the capacity of the desiccant chamber. The desiccant material (contained within the desiccant pouch) and the chamber within which it is positioned, would be separately disposable apart from the motor/pump section and the power section of the device.

The device of this second embodiment would also lend itself to the use of more complex automated decision algorithms that may serve to control the airflow rates and respond to changes in pressure within the system. This increased electronic control complexity also allows the second embodiment described to lend itself to the greater use of sensors within the system that would monitor the various pressures, fluid content, and blood composition (oxygen saturation, for example). A number of such sensor applications are described in U.S. Pat. No. 6,648,862, incorporated by reference above.

2. The Chest Tube & Chest Tube Terminus

Figure 5:
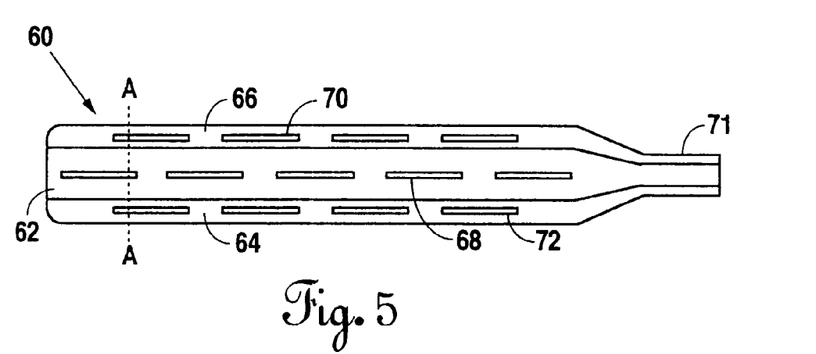
FIG. 5 is a top view of a first chest tube terminus structure of the system of the present invention.
Figure 6A:
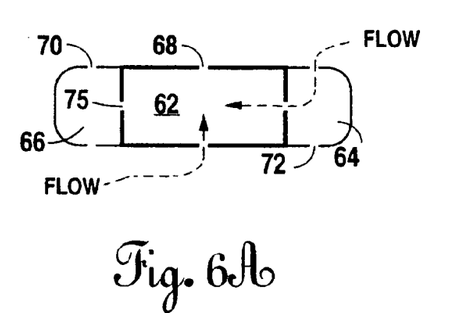
FIG. 6A is a transverse cross-sectional view (along A-A in FIG. 5) of the first chest tube terminus structure of the system of the present invention shown in FIG. 5.

As indicated above, many problems with chest tubes have centered around blood coagulating in the tube and blocking the flow of air and fluid through the tube. The present invention provides a solution to this problem in the form of a combination high-flow/low-flow tube design that incorporates low-flow or "dead tubes" that allow the blood to collect within them without blocking the high-flow portion of the tube. An example of one such tube and terminus structure is illustrated in FIG. 5 (top view), FIGS. 6A & 6B (transverse cross-section views) and FIGS. 6C & 6D (lateral cross-sectional views). As shown in FIG. 5, this chest tube terminus has a central, relatively large, high-flow lumen 62 and two smaller low-flow lumens 64 & 66 on either side. In a first variation of the structure shown, all of the lumens may be connected to the suction device with the individual lumen air flow rate determined by the differences in cross-sectional geometry of the lumens (and the opening of the lumen into the tube) as well as the number and size of the fenestrations positioned through the lumen walls. This structure shown in transverse cross-section in FIG. 6A is functionally disclosed in clear detail in the lateral cross-section of FIG. 6C. As shown, flow can occur directly from the low flow lumens into the suction tube in addition to flowing first into the high flow lumen (through the intermediate fenestrations 75) and then into the suction tube 73.

Each of the lumens is preferably perforated with a plurality of external fenestrations as shown; high flow lumen 62 with fenestrations 68, low flow lumen 64 with fenestrations 72, and low flow lumen 66 with fenestrations 70. Additional intermediate fenestrations 75 may be incorporated that would allow the low-flow lumens to communicate with the high-flow lumen as described above. In any of these variations, the structures as shown and described serve to maintain the free flow of air through the system. As collected blood and other fluids coagulate, the coagulated components tend to migrate into the low-flow lumens and thereby leave the high-flow lumen unobstructed for continuous airflow. In addition, the fenestrations provide multiple pathways for air to move around a blood clot in the tube and thereby facilitate continuous airflow.

Figure 6B:
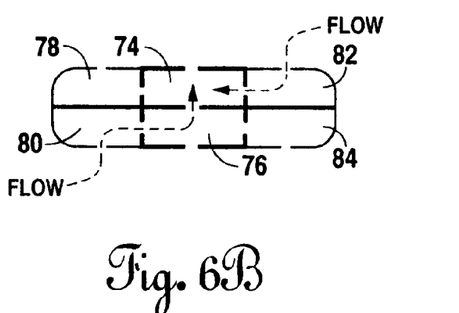
FIG. 6B is a transverse cross-sectional view of an alternate configuration to the chest tube terminus structure of the system of the present invention shown in FIG. 5.
Figure 6C:
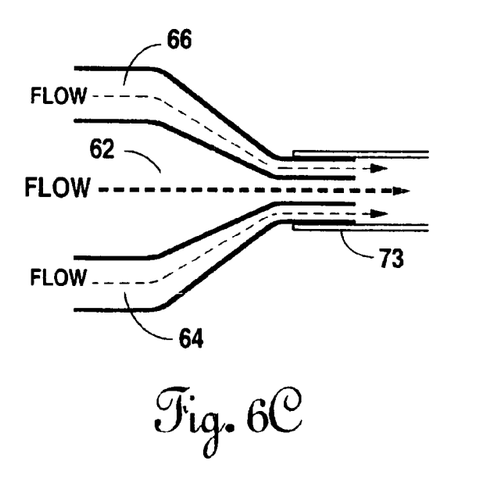
FIG. 6C is a top cross-sectional view of the first chest tube terminus structure of the system of the present invention shown in FIG. 6A at its attachment to the chest tube.
Figure 6D:
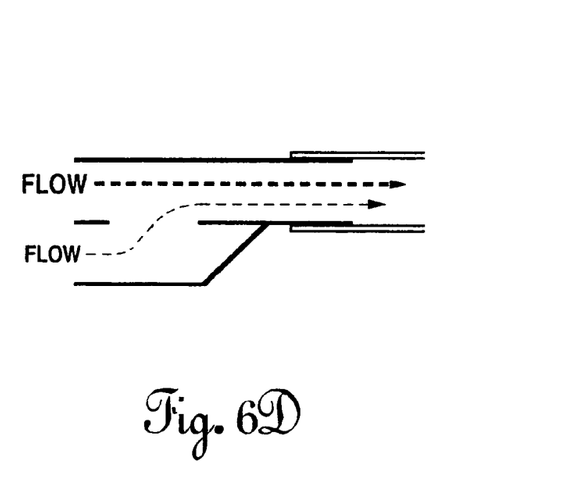
FIG. 6D is a side cross-sectional view of the chest tube terminus structure of the system of the present invention shown in FIG. 6B at its attachment to the chest tube.

Alternatively, as illustrated in FIG. 6B, a chest tube in accordance with the present invention may have one or more "live" lumens 74, 78 & 82, connected to the suction source and one or more "dead" lumens 76, 80 & 84 that are not directly connected to the suction source. The "live" lumens 74, 78 & 82 are connected by intermediate fenestrations (as shown) to the "dead" lumens 76, 80 & 84, which serve as reservoirs for the suctioned liquid, leaving the "live" lumens 74, 78 & 82 clear for continuous airflow. FIG. 6D discloses in a lateral cross-sectional view the manner in which the "dead" lumens terminate prior to the suction tube connection point leaving only the "live" lumens to directly connect with the suction tube.

Figure 7A:
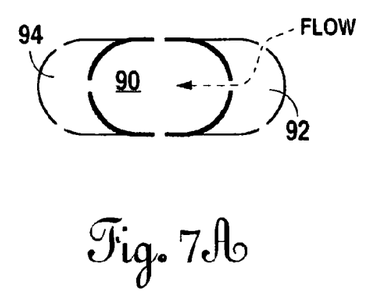
FIGS. 7A, 7C, and 7E are transverse cross-sectional views of further alternate embodiments of the chest tube terminus structure of the system of the present invention.
Figure 7B:
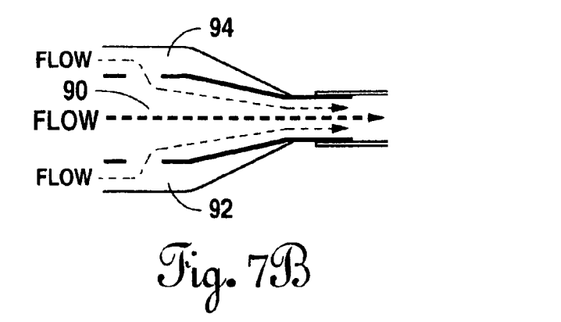
FIGS. 7B, 7D, and 7F are top and side cross-sectional views of the further alternate embodiments of the chest tube terminus structure of the system of the present invention as shown in FIGS. 7A, 7C, and 7E respectively.

Referring now to FIG. 7A, a further alternative preferred chest tube design in accordance with the present invention is shown in cross-section to comprise a centralized, relatively stiff, high-flow lumen 90 and one or more peripheral low-flow lumens 92 & 94 formed of relatively flexible outer walls that collapse as blood coagulates in them. The collapse of the outer, flexible lumens 92 & 94 helps to push the liquid through the chest tube and into the desiccant chamber of the suction device. FIG. 7B discloses the manner of connection to the suction tube wherein low flow lumens 92 & 94 terminate prior to the suction tube connection leaving only high flow lumen 90 directly connected to the suction tube. In this manner, flow through the low flow lumens is restricted through the intermediate fenestrations into the high flow lumen, thus resulting in the lower flow and the desired accumulation of fluids and coagulates in the side lumens.

Figure 7C:
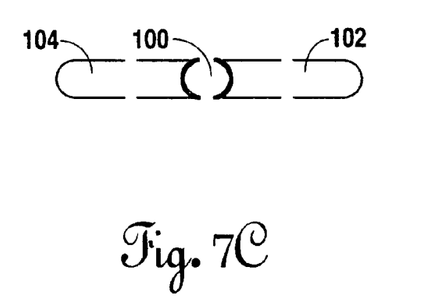
Figure 7D:
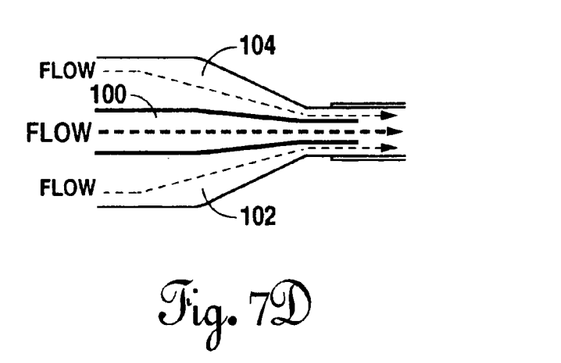

Referring now to FIG. 7C, still another alternative preferred embodiment of a chest tube design in accordance with the present invention comprises a central suction lumen 100 and one or more diffused suction lumens 102 & 104, each of which may be connected to a different level of suction (via different ports on the suction device connected to the respective lumens/lines (not shown)) or the same level of suction as shown in FIG. 7D. In this structure, with the different levels of suction, blood clots will again tend to congregate in the lower-suction lumens 102 & 104, leaving the higher-suction lumen 100 free for continued airflow.

Figure 7E:
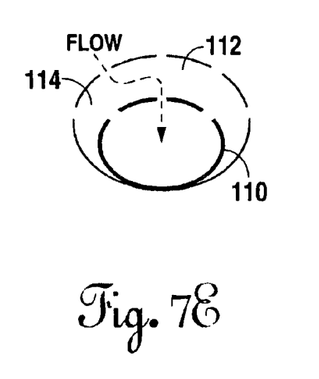
Figure 7F:
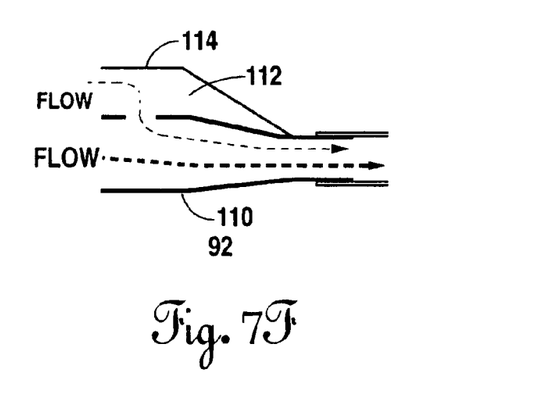

Still another alternate preferred embodiment of the cross-sectional structure of the chest tube component of the present invention is shown in FIGS. 7E & 7F. In this embodiment, a central fenestrated suction tube 110 is surrounded by an outer tube 114, with dead space 112 in between the two tubes. In this embodiment, suction that is placed on inner tube 110 allows fluids to be drawn up into the tube and then deposited through the fenestrations (as shown) into the dead space 112 in between inner tube 110 and outer tube 114. FIG. 7F shows the manner in which this embodiment is connected to the suction tube with only the central tube 110 directly connected.

The multi-lumen structures described above also lend themselves to utilization of certain two-way airflow configurations and methods that could be used to help keep the tubes clear of fluids. The basic principles of a two-way airflow are known in the art and have been utilized with mixed success in conjunction with known suction devices and known drainage catheters. An example of the application of the basic principle is described in U.S. Pat. No. 5,738,656. As long as the overall functional effect of the chest tube structure and the suction system is to create a sub-atmospheric pressure (suction) within the intrapleural space, such two-way air-flow could direct and allow a constant flow of air through the tubes to keep them clear. Unique applications of the two-way air flow approach could, for example, be implemented in the present invention by alternately reversing the "live" and "dead" lumens in the multi-lumen configurations described above. In a first state, deposits would tend to form in the "dead" chambers and in particular in the fenestrations connecting to the "live" chambers. In a reverse state these same deposits could be "cleared" from the fenestrations when the airflow across the fenestrations is reversed. Such flow reversal could be accomplished by using a valve located at the chest tube terminus or by bringing separate suction tubes or tube lumens back to the suction device where the switching could occur. Other approaches that implement a reversal of pressure differentials across the fenestrations may also serve to clear the tube of blockages.

Figure 8:
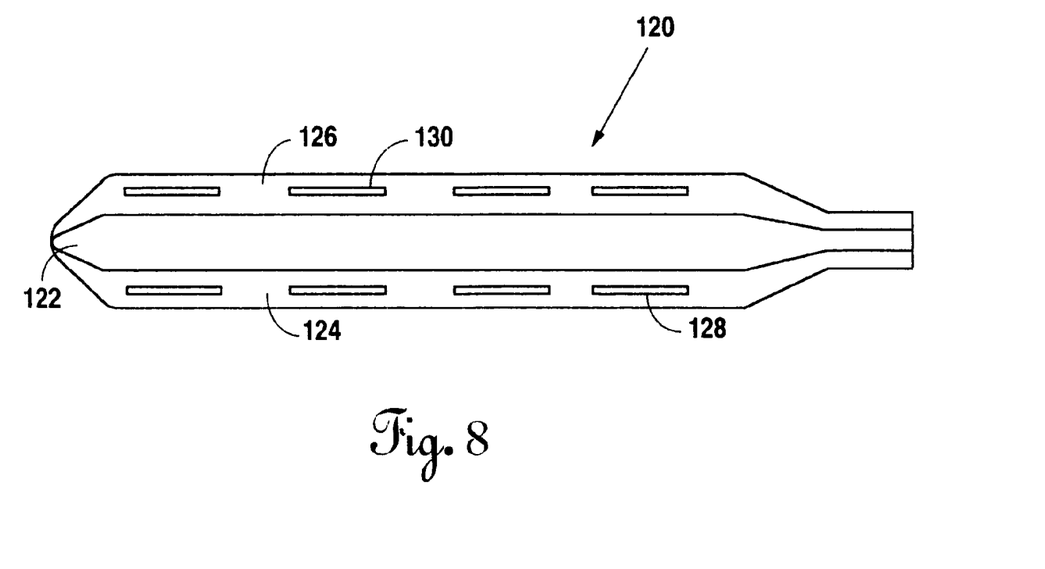
FIG. 8 is a top view of a further alternate chest tube terminus structural embodiment of the system of the present invention.
Figure 9:
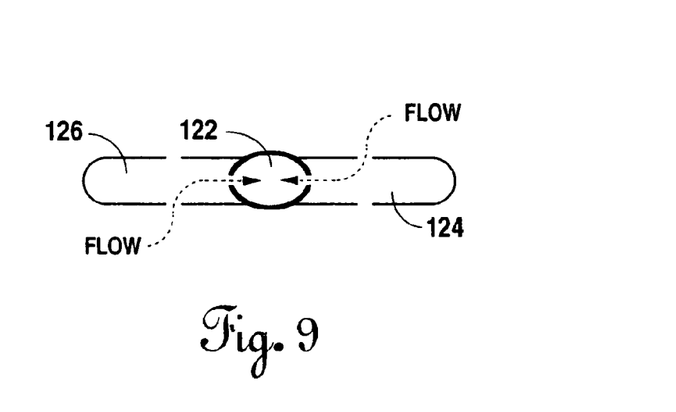
FIG. 9 is a transverse cross-sectional view of the chest tube terminus embodiment of the system of the present invention shown in FIG. 8.

Referring now to FIGS. 8 & 9, still another embodiment is shown having a central high flow lumen 122 with fenestrations (hidden in this view, interior to the structure) and diffusion areas or low flow lumens 124 & 126 on either side, each with their own fenestrations 128 & 130 to the outside. In this embodiment, internally fenestrated central tube 122 would be of the same stiffness as currently available chest tubes. Central tube 122 is bordered by lumens 124 & 126 formed by a softer rubber material, which serves to define diffusion areas within. The chest tube terminus 120 thus defined, including side lumens 124 & 126 constructed of the softer material, may be readily inserted into the intrapleural space with a trocar removably positioned down the central tube 122.

Figure 10:
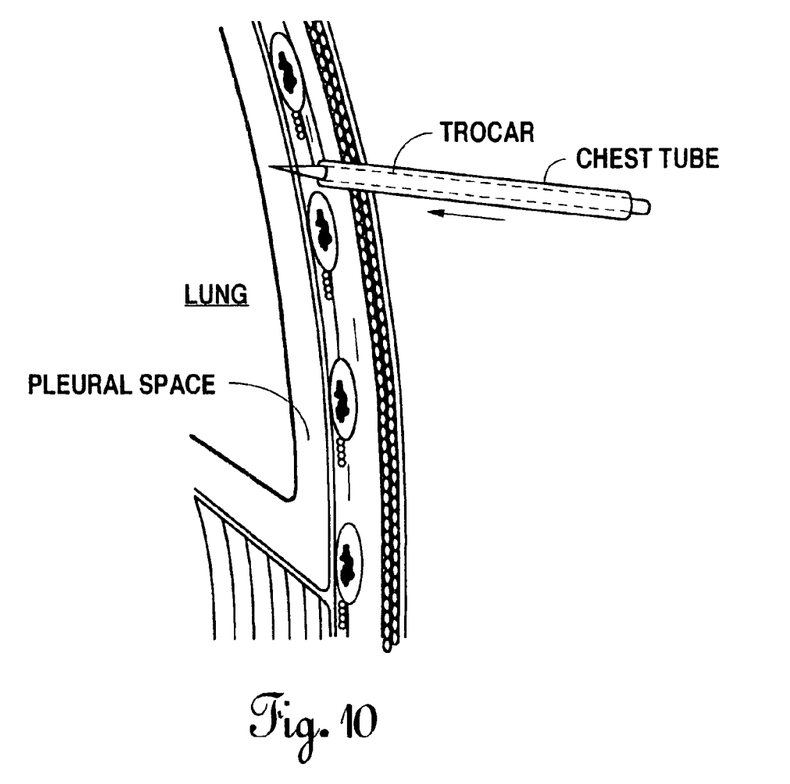
FIG. 10 is a schematic cross-sectional view of the human chest showing the typical placement of a chest tube using a trocar.
Figure 11:
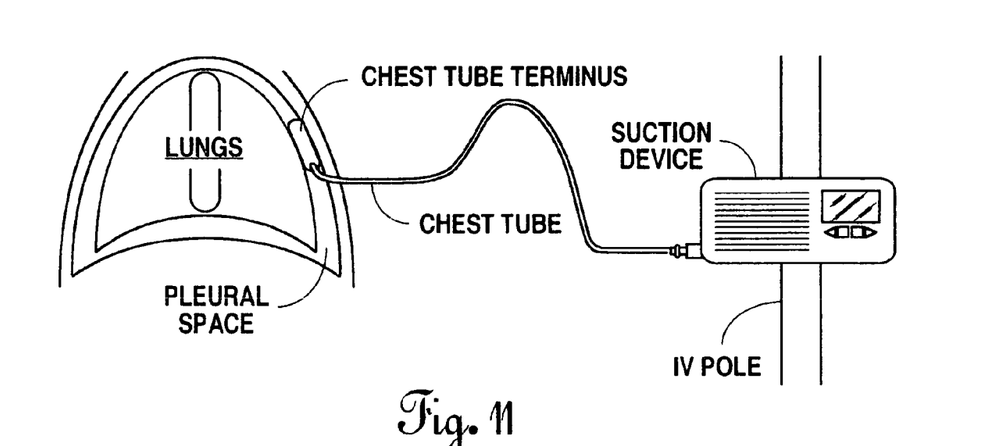
FIG. 11 is a schematic diagram showing the placement and use of the primary components of the chest tube drainage system of the present invention.

FIG. 10 describes in broad terms the manner of insertion of a drainage chest tube through the use of a trocar as is known in the art. FIG. 11 shows in broad terms the arrangement of the basic components of the chest tube drainage system of the present invention and its placement within the chest of a patient.

3. Further Alternate Configurations of the Suction Device

Figure 12:
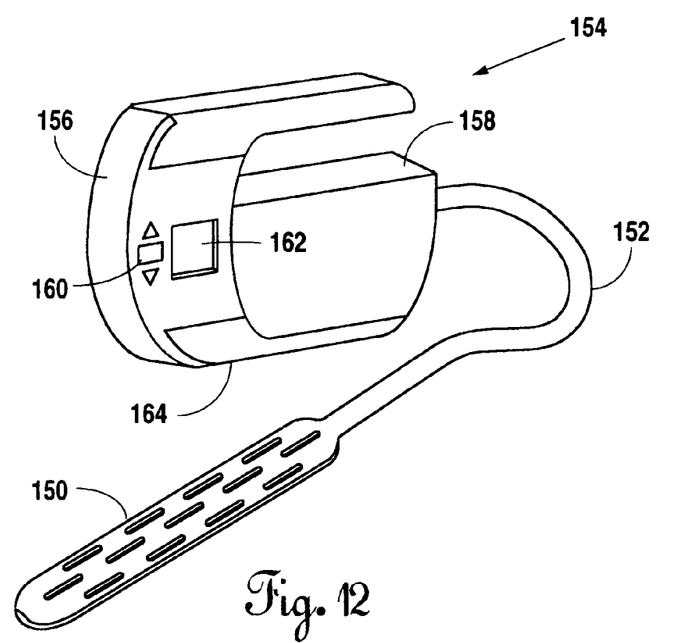
FIG. 12 is a perspective view of a further alternate embodiment of the system of the present invention.

Reference is now made to FIGS. 12-15 for a brief description of an alternate structural embodiment of the system of the present invention. In FIG. 12, suction device 154 is shown incorporating desiccant chamber 158, which itself is connected by way of chest tube 152 to chest tube terminus 150. Suction device 154 is seen to comprise pump/motor section 156, as well as power supply 164. Pump/motor section 156 incorporates flow controls 160 and data display 162. The embodiment shown in FIG. 12 lends itself to greater mobility and ease of use by the health care providers attending to the patient utilizing the chest tube drainage system.

Figure 13:
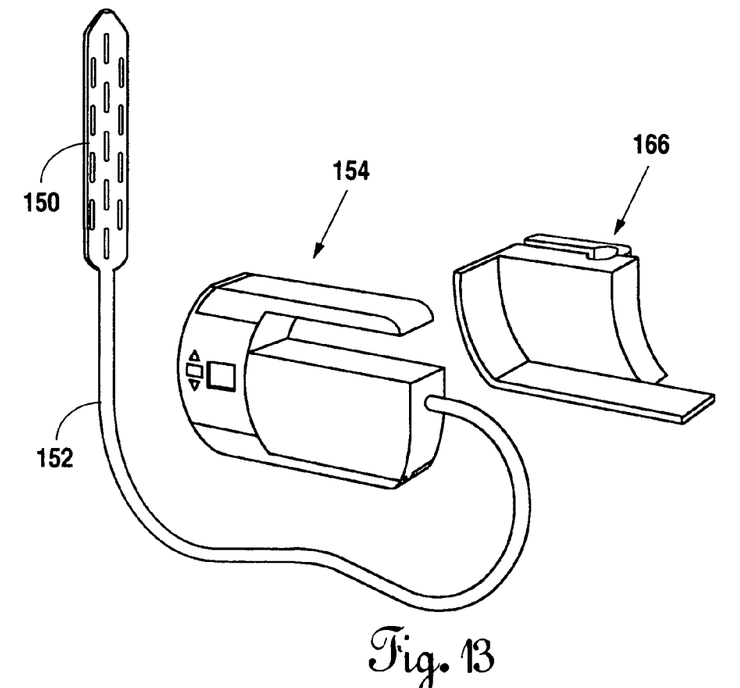
FIG. 13 is a perspective view of the embodiment of the system of the present invention shown in FIG. 12 with the addition of a power charger unit.
Figure 14:
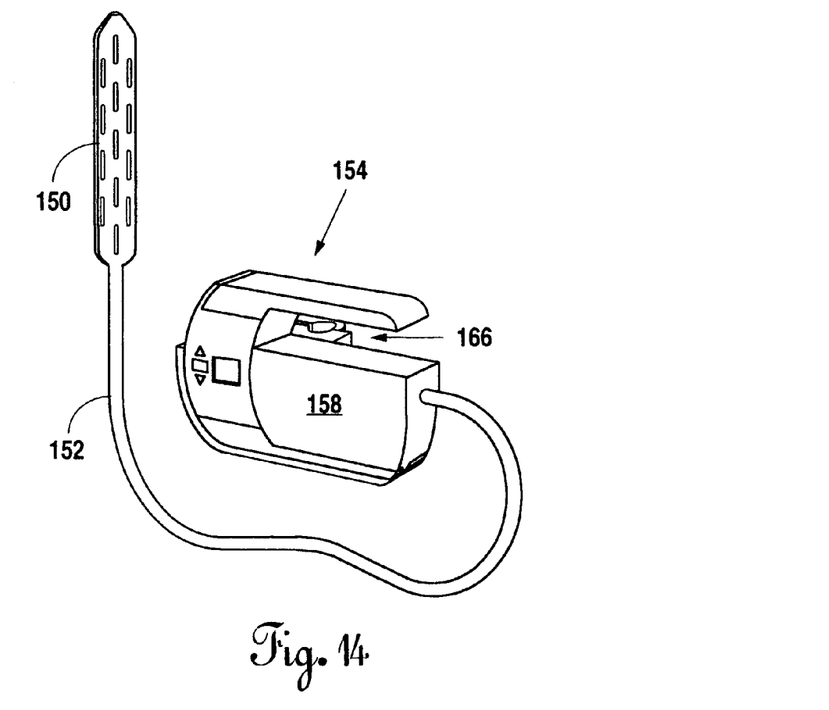
FIG. 14 is a perspective view of the embodiment of the system of the present invention shown in FIG. 12 with the power charger unit attached.

FIG. 13 shows the system described above in FIG. 12 with the addition of battery charger and mounting bracket 166. The structure of charger and bracket 166 is such as to receive suction device 154 therein and provide a charge to incorporated power supply 164. This attachment is shown in clearer detail in FIG. 14 where suction device 154 is slid into and electrically connected with battery charger and mounting bracket 166. Bracket 166 may incorporate features on a reverse side that would permit it to be mounted to an IV pole as in the previously described embodiments.

Figure 15:
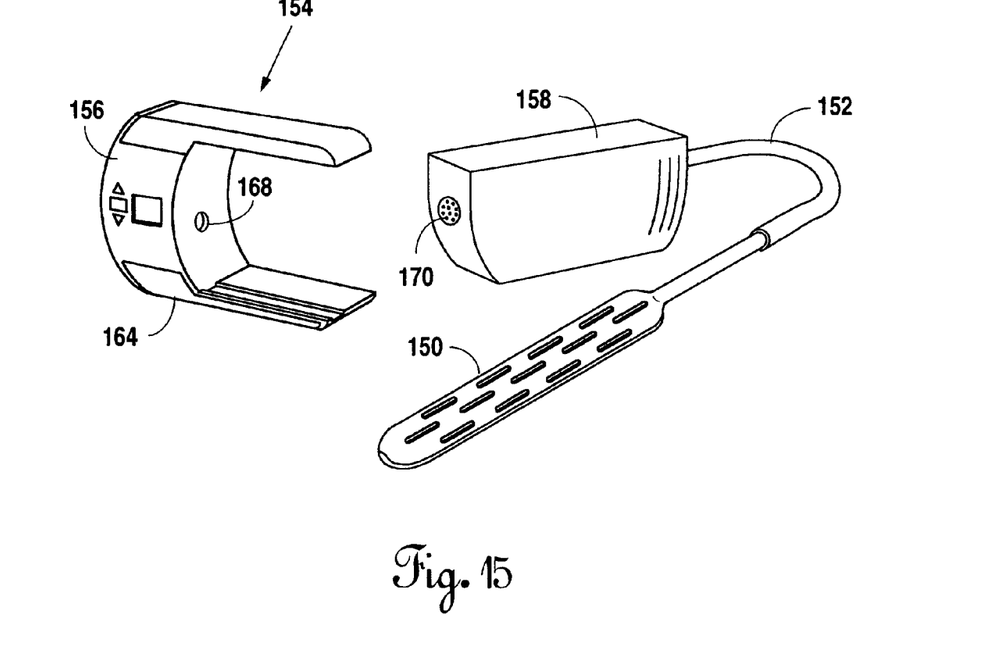
FIG. 15 is a perspective view of the embodiment of the system of the present invention shown in FIG. 12 with the desiccant chamber detached.

Reference is finally made to FIG. 15 wherein desiccant chamber 158 is shown removed from suction device 154. In this view, vacuum ports 168 and 170 are shown on suction device 154 and desiccant chamber 158 respectively. When attached together, these ports 168 and 170 mate to form the connection between suction device 154 and desiccant chamber 158. In this manner, the assembly comprising desiccant chamber 158, chest tube 152, and chest tube terminus 150, may all be disposed of separately. In some instances it may be appropriate to dispose of desiccant chamber 158 alone once it becomes full, while not immediately removing or disposing of chest tube 152 and chest tube terminus 150.

Figure 16:
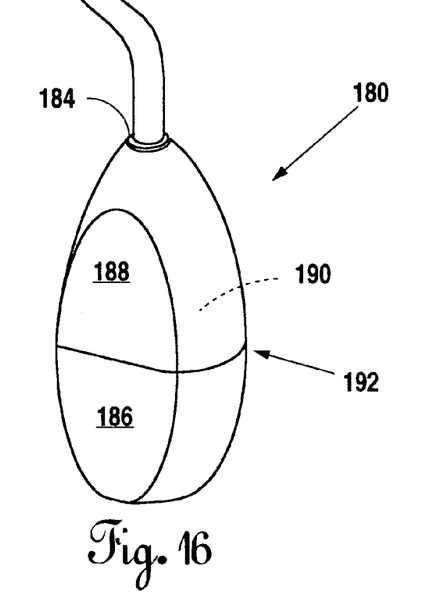
FIG. 16 is a perspective view of a further alternate embodiment of suction device of the system of the present invention.
Figure 17:
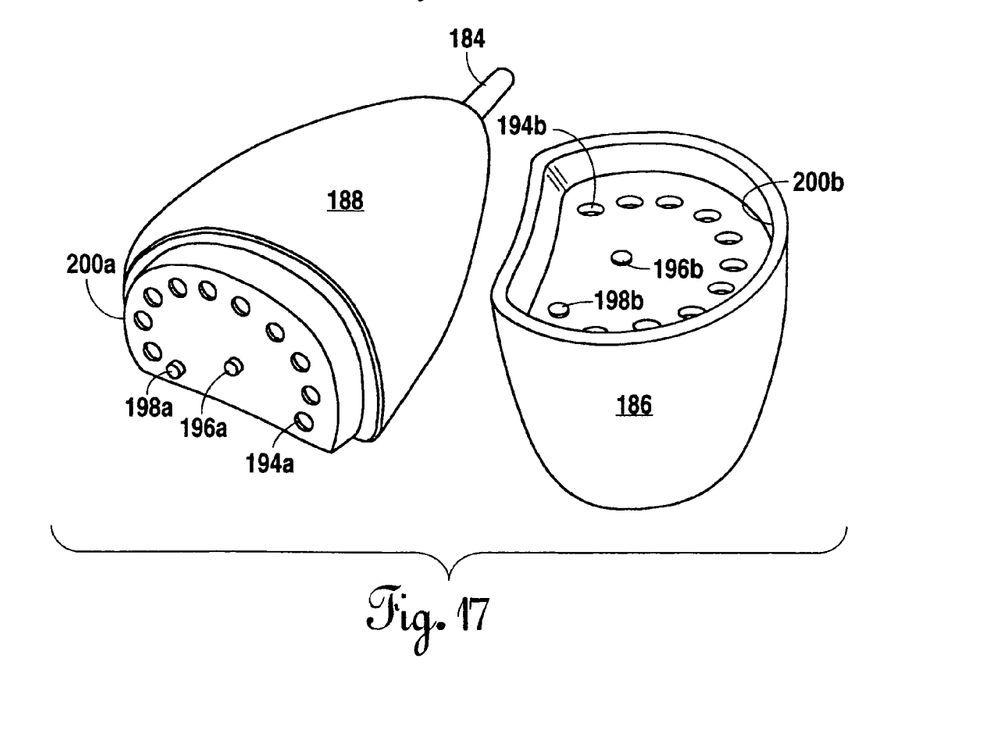
FIG. 17 is a perspective view of the embodiment of the system of the present invention shown in FIG. 16 with the desiccant chamber and the pump/motor unit detached from each other.
Figure 18:
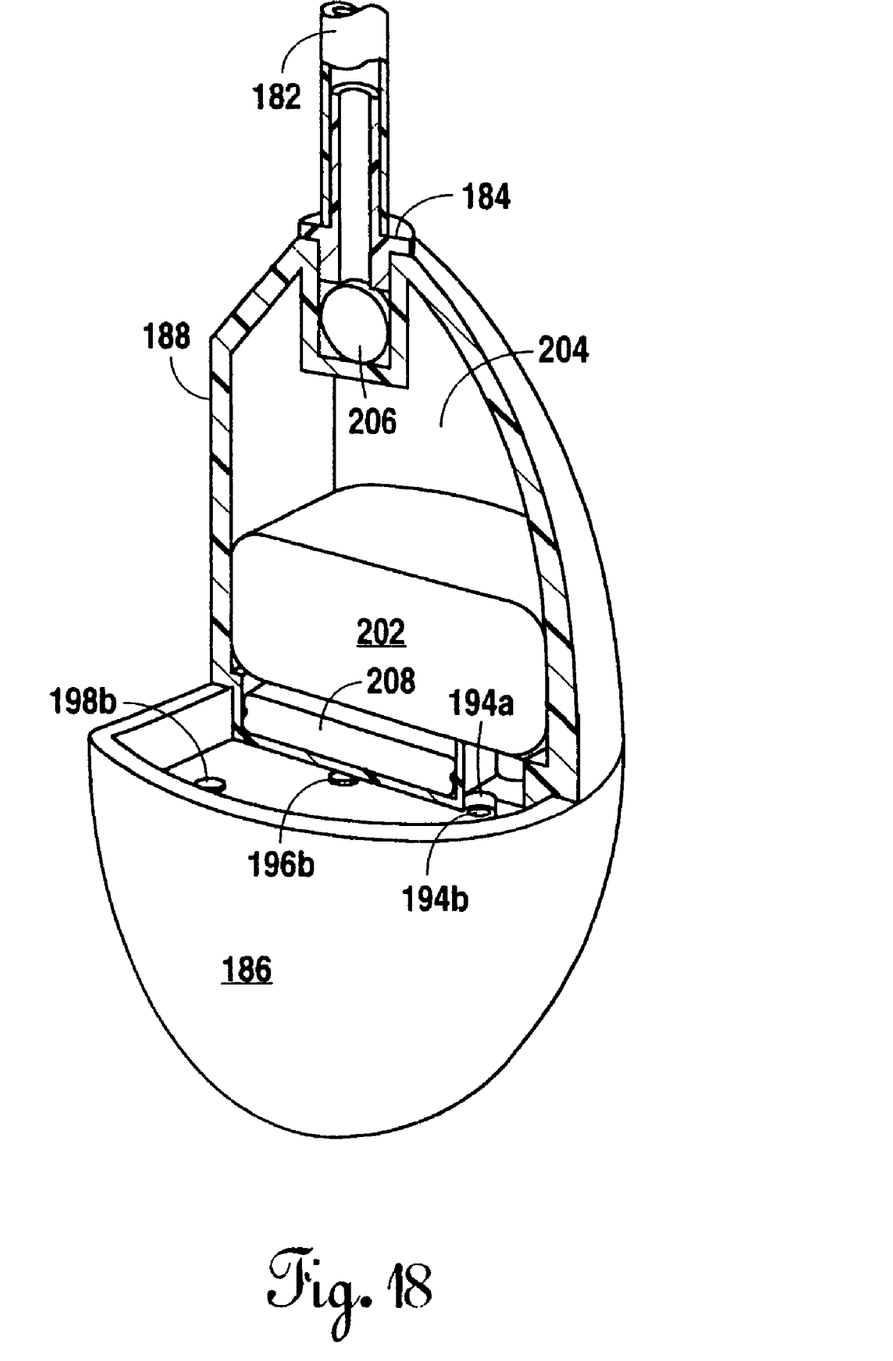
FIG. 18 is a partial cross-sectional perspective view of the embodiment of the system of the present invention shown in FIG. 16.

Reference is now made to FIGS. 16-18 for a brief description of a further alternative embodiment of the suction device described for the system of the present invention. Suction device 180, shown in FIG. 16, is similar in many respects to the embodiment disclosed above in conjunction with FIG. 1. Suction device 180 is connected to chest tube 182 by way of chest tube connector 184, which is positioned at a top point on desiccant chamber 188. Desiccant material 190 is shown contained within desiccant chamber 188 in FIG. 16. Motor/Pump section 186 is shown attached to desiccant chamber 188 at disconnection point 192.

FIG. 17 shows in greater detail the interior components and structure of suction device 180 described above with respect to FIG. 16. In this view, desiccant chamber 188 has been removed from motor/pump section 186 at disconnection point 192. Various features along this connection point 192 are designed to match and mate when the assembly is connected. Vacuum ports 194a in desiccant chamber 188 align with and match vacuum ports 194b in motor/pump section 186. Desiccant chamber 188 incorporates a pressure sensor (described in more detail below with regard to FIG. 18) which electrically connects into motor/pump section 186 by way of contacts 196a/196b and 198a/198b. Desiccant chamber 188 incorporates a reduced perimeter 200a that fits into and locks onto track 200b positioned on the upper perimeter of suction device 186. When connected in this way, each of the respective vacuum ports and electrical contacts align for connection between the components of the device.

Reference is finally made to FIG. 18 for a detailed description of the interior construction of desiccant chamber 188 and its respective connections to motor/pump section 186. In this partial cross sectional view of FIG. 18, desiccant material 202 is shown positioned within the volume of space 204 defined by the walls of desiccant chamber 188. Tube connector 184 is shown to incorporate a check valve 206 to prevent the back-flow of material from chamber 188 into chest tube 182. Aligned ports 194a and 194b are shown in this view, as are aligned contacts 196a/196b and 198a/198b.

Shown positioned below desiccant material 202 in FIG. 18 is differential pressure transducer 208. This transducer provides the necessary determination of the content of desiccant chamber 188 and serves to alert a health care provider when the chamber has been filled and needs to be replaced.

4. Additional Features and Additional Embodiments

A variety of sensors may also be utilized in association with the chest tube embodiments constructed in accordance with the present invention. For example, flow rate, $SAO_2$, ECG, and respiratory rate sensors could be incorporated into the chest tube at a variety of appropriate locations. Pressure sensors, both absolute and differential, could be placed at various locations within the airflow path of the full system to permit accurate monitoring and control over the function of the drainage system. These sensors serve to reduce the level of human monitoring that might otherwise be required and supplement such human monitoring to provide better patient care.

Additionally, embedded web-enabled sensor and monitoring technologies could be placed in the various devices of the present invention to transmit the data collected to a remote location via the Internet. Such systems, typically housed within the suction device of the present system, could serve to alert the health care providers of both critical and non-critical conditions within the patient.

It is anticipated that further variations in both the structure of the suction device of the present invention and the chest tube terminus of the present invention will be apparent to those skilled in the art after a reading of the present disclosure and a discernment of the attached drawing figures. Such variations, while not explicitly described and defined herein, may be seen to fall within the spirit and scope of the present invention.

I claim:

1. A suction device comprising:
   a pump operatively connected to a power supply;
   a desiccant material in a desiccant chamber fluidly connected to the pump;
   a tube fluidly connected to the desiccant chamber through a tube connection;
   a terminus having a first lumen and a second lumen fluidly connected to the tube on an end opposite the tube connection, the first lumen and the second lumen sharing a same wall; and
   a plurality of fenestrations positioned through the first lumen and the second lumen to allow air and liquid to flow between the first lumen and the second lumen;
   wherein the first lumen is larger than the second lumen to permit a higher flow rate in the first lumen than in the second lumen.

2. The suction device of claim 1, wherein said desiccant chamber contains anti-microbial and/or anti-bacterial chemicals able to render suctioned air and liquids non-bio-hazardous.

3. The suction device of claim 1, wherein said desiccant chamber is constructed of clear, high impact plastic.

4. The suction device of claim 1, wherein said desiccant chamber is removably attachable to said pump.

5. The suction device of claim 1, wherein said tube connection allows said tube to be removably connectable to said desiccant chamber.

6. The suction device of claim 5, wherein said tube connection is a screw-on or quick connect fitting.

7. The suction device of claim 1, further comprising a trocar attached to the tube on the end opposite the tube connection.

8. The suction device of claim 1, wherein said pump creates suction through said tube.

9. The suction device of claim 8, wherein said first lumen and said second lumen are in direct communication with said pump.

10. The suction device of claim 8, wherein said first lumen is in direct communication with said pump, and said second lumen is in indirect communication with said pump.

11. The suction device of claim 8, wherein said first lumen comprises inflexible walls, and said second lumen comprises flexible walls.

12. The suction device of claim 8, wherein said suction in said first lumen is greater than said suction in said second lumen.

13. The suction device of claim 12, wherein said tube further comprises a plurality of low-flow lumens, each connected to said pump and each of said plurality of low-flow lumens capable of having an individual suction level.

14. The suction device of claim 1, wherein said terminus comprises a central suction tube and a dead space in an interior of said terminus, wherein said central suction tube has fenestrations between said central suction tube and said dead space that allow communication between said central suction tube and said dead space.

15. The suction device of claim 1, wherein said tube further comprises one or more sensors.

16. The suction device of claim 15, wherein said one or more sensors are chosen from flow rate, pressure, oxygen saturation, electrocardiogram, and respiratory rate sensors.

17. The suction device of claim 15, wherein said one or more sensors are remotely monitorable.

18. A suction device comprising:
   a pump operatively connected to a power supply;
   a desiccant material in a desiccant chamber fluidly connected to the pump;
   a tube fluidly connected to the desiccant chamber through a tube connection; and
   a terminus having a first lumen and a second lumen fluidly connected to the tube on an end opposite the tube connection, the first lumen and the second lumen sharing a same wall;
   wherein said first and second lumens comprise a central suction tube and a dead space in an interior of said terminus, wherein said central suction tube has fenestrations between said central suction tube and said dead space that allow communication between said central suction tube and said dead space.

19. The suction device of claim 18, wherein said desiccant chamber contains anti-microbial and/or anti-bacterial chemicals able to render suctioned air and liquids non-bio-hazardous.

20. The suction device of claim 18, wherein said desiccant chamber is constructed of clear, high impact plastic.

21. The suction device of claim 18, wherein said desiccant chamber is removably attachable to said pump.

22. The suction device of claim 18, wherein said tube connection allows said tube to be removably connectable to said desiccant chamber.

23. The suction device of claim 22, wherein said tube connection is a screw-on or quick connect fitting.

24. The suction device of claim 18, further comprising a trocar attached to the tube on the end opposite the tube connection.

25. The suction device of claim 18, wherein said pump creates suction through said tube.

26. The suction device of claim 25, wherein said first lumen and said second lumen are in direct communication with said pump.

27. The suction device of claim 25, wherein said first lumen is in direct communication with said pump, and said second lumen is in indirect communication with said pump.

28. The suction device of claim 25, wherein said first lumen comprises relatively inflexible walls, and said second lumen comprises relatively flexible walls.

29. The suction device of claim 25, wherein said suction in said first lumen is greater than said suction in said second lumen.

30. The suction device of claim 29, wherein said tube further comprises a plurality of low-flow lumens, each connected to said pump and each of said plurality of low-flow lumens capable of having an individual suction level.

31. The suction device of claim 18, wherein said tube further comprises one or more sensors.

32. The suction device of claim 31, wherein said one or more sensors are chosen from flow rate, pressure, oxygen saturation, electrocardiogram, and respiratory rate sensors.

33. The suction device of claim 31, wherein said one or more sensors are remotely monitorable.

34. The suction device of claim 18, wherein the terminus has a plurality of lumens, and wherein the plurality of lumens includes the first lumen and the second lumen.

35. The suction device of claim 1, wherein the terminus has a plurality of lumens, and wherein the plurality of lumens includes the first lumen and the second lumen.

* * * * *